US009527803B2

(12) United States Patent
Huang et al.

(10) Patent No.: US 9,527,803 B2
(45) Date of Patent: Dec. 27, 2016

(54) CRYSTAL FORM VII OF AGOMELATINE, PREPARATION METHOD AND USE THEREOF AND PHARMACEUTICAL COMPOSITION CONTAINING SAME

(75) Inventors: Yu Huang, Shanghai (CN); Ling Tong, DongGuan (CN); Xueyan Zhu, Shanghai (CN); Hanbin Shan, Gaoan (CN); Zhedong Yuan, Shanghai (CN); Xiong Yu, Hongkou District (CN)

(73) Assignees: LES LABORATOIRES SERVIER, Suresnes Cedex (FR); SHANGHAI INSTITUTE OF PHARMACEUTICAL INDUSTRY, Jing'an District, Shanghai (CN)

( * ) Notice: Subject to any disclaimer, the term of this patent is extended or adjusted under 35 U.S.C. 154(b) by 0 days.

(21) Appl. No.: 14/006,468

(22) PCT Filed: Mar. 22, 2012

(86) PCT No.: PCT/CN2012/072816
§ 371 (c)(1),
(2), (4) Date: Sep. 20, 2013

(87) PCT Pub. No.: WO2012/126385
PCT Pub. Date: Sep. 27, 2012

(65) Prior Publication Data
US 2014/0011883 A1  Jan. 9, 2014

(30) Foreign Application Priority Data

Mar. 23, 2011 (CN) .......................... 2011 1 0070828

(51) Int. Cl.
C07C 231/24 (2006.01)
C07C 233/22 (2006.01)
A61K 9/48 (2006.01)

(52) U.S. Cl.
CPC .......... *C07C 233/22* (2013.01); *A61K 9/4866* (2013.01); *C07C 231/24* (2013.01)

(58) Field of Classification Search
CPC .... C07C 233/18; C07C 231/24; C07C 233/10; A61K 31/165
See application file for complete search history.

(56) References Cited

U.S. PATENT DOCUMENTS

| | | | |
|---|---|---|---|
| 7,498,466 B2 * | 3/2009 | Souvie et al. ................ | 564/172 |
| 2006/0270877 A1 * | 11/2006 | Coquerel et al. ............ | 564/219 |
| 2012/0004313 A1 | 1/2012 | Shan et al. | |

FOREIGN PATENT DOCUMENTS

| | | |
|---|---|---|
| AU | 2006203340 | 8/2006 |
| CN | 1907957 | 2/2007 |

(Continued)

OTHER PUBLICATIONS

B. Tinant, et al. Acta Cryst,1994, C50, p. 907-910.

(Continued)

*Primary Examiner* — Marcos Sznaidman
*Assistant Examiner* — Rayna B Rodriguez
(74) *Attorney, Agent, or Firm* — Hueschen and Sage

(57) ABSTRACT

The present invention provides a new crystalline form VII of agomelatine, its method of preparation, application and pharmaceutical composition. This new crystalline form offers high purity, a stable crystalline structure and good reproducibility, while its method of production lends itself well to large scale production. In terms of stability and purity, it is superior to the numerous crystalline forms which have hitherto been reported. As a result, the crystalline form VII of the present invention possesses advantages in pharmaceutical preparation.

12 Claims, 5 Drawing Sheets

(56) References Cited

FOREIGN PATENT DOCUMENTS

| CN | 101781225 | 7/2009 |
|----|-----------|--------|
| CN | 101585779 | 11/2009 |
| CN | 101704763 | 5/2010 |
| CN | 101792400 | 9/2010 |
| CN | 101921205 | 12/2010 |

OTHER PUBLICATIONS

International Search Report for PCT/CN2012/072816.
IInternational Preliminary Report on Patentability Issued Sep. 24, 2013 for PCT/CN2012/072816.

* cited by examiner

| # | 2θ° | d(Å) | Relative intensity |
|---|---|---|---|
| 1 | 8.636 | 10.2303 | 0.43 |
| 2 | 10.557 | 8.3725 | 32.35 |
| 3 | 13.301 | 6.6509 | 11.45 |
| 4 | 13.893 | 6.3691 | 5.74 |
| 5 | 16.145 | 5.4855 | 10.60 |
| 6 | 17.286 | 5.1258 | 6.19 |
| 7 | 17.841 | 4.9675 | 100.00 |
| 8 | 18.594 | 4.7681 | 0.76 |
| 9 | 19.359 | 4.5813 | 10.83 |
| 10 | 20.089 | 4.4164 | 11.77 |
| 11 | 21.216 | 4.1843 | 3.17 |
| 12 | 23.366 | 3.8040 | 29.82 |
| 13 | 24.944 | 3.5667 | 21.60 |
| 14 | 26.128 | 3.4078 | 12.47 |
| 15 | 26.482 | 3.3630 | 3.86 |
| 16 | 28.398 | 3.1402 | 2.24 |
| 17 | 29.583 | 3.0172 | 5.26 |
| 18 | 30.252 | 2.9519 | 3.12 |
| 19 | 30.510 | 2.9276 | 4.94 |
| 20 | 31.715 | 2.8190 | 0.27 |

| 21 | 32.995 | 2.7125 | 2.44 |
| 22 | 34.457 | 2.6007 | 2.57 |
| 23 | 36.152 | 2.4825 | 1.10 |
| 24 | 39.647 | 2.2714 | 1.45 |
| 25 | 43.533 | 2.0772 | 1.16 |

Figure 1 (cont.)

CRYSTAL FORM VII OF AGOMELATINE, PREPARATION METHOD AND USE THEREOF AND PHARMACEUTICAL COMPOSITION CONTAINING SAME

TECHNICAL FIELD

The present invention relates to a new crystalline form of agomelatine, N-[2-(7-methoxy-1-naphthyl)ethyl]acetamide, its method of preparation, application and pharmaceutical compositions.

PRIOR ART

Agomelatine, with chemical name N-[2-(7-methoxy-1-naphthyl)ethyl]acetamide and brand name Valdoxan, has the following chemical structure (I):

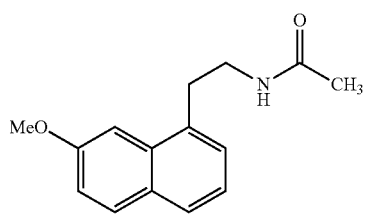

It has a dual effect, acting not only as an agonist of melatoninergic system receptors, but also as an antagonist of the $5HT_{2C}$ receptor. Its properties mean that it is active in the central nervous system, especially in the treatment of severe depression, seasonal affective disorder, sleep disorders, cardiovascular diseases, digestive system diseases, insomnia and fatigue brought on by jet lag, eating disorders and obesity. Agomelatine is the first melatoninergic antidepressant, and is effective in the treatment of depression and the improvement of sleep parameters, while not affecting sexual function.

The preparation and therapeutic use of agomelatine have been reported in the European patent EP0447285.

In view of the pharmaceutical value of the said compound, it is important to obtain a highly pure, stable crystalline form with good reproducibility in order for it to be advantageous in pharmaceutical preparation and stable enough for long-term storage without having specific requirements in terms of temperature, light, humidity or oxygen levels.

The Chinese patents CN200510071611.6, CN200610108396.7, CN200610108394.8, CN200610108395.2, CN200910047329.2, CN200910245029.5 have made public the various crystalline forms as well as the preparation methods of agomelatine.

Among these, crystalline form II is prepared by recrystallization from ethanol and water. Crystalline form III is prepared by heating agomelatine to 110° C. until complete melting occurs and then slowly cooling down until crystallization takes place. Crystalline form IV is prepared by heating agomelatine at 110° C. until complete melting occurs and then rapidly cooling down to 50-70° C. and maintaining a temperature of 70° C. for approximately 5 hours until crystallization occurs; crystalline form V is prepared by the so-called "high energy" mechanical grinding of agomelatine, while crystalline form VI is obtained through recrystallization from acetic acid and water.

It is well known that chemical compounds can display different molecular arrangements, and possess different solid forms, i.e. there are many crystalline forms of the same compound. Among pharmaceuticals, different crystalline forms can lead to differences in dissolution and bioavailability. Therefore in pharmaceutical development it is particularly important to search for crystalline structures that are highly pure, offer good reproducibility, are easy to produce and use, and with excellent dissolution and bioavailability.

SCOPE OF THE INVENTION

The aim of the present invention is to provide a new crystalline form of agomelatine, i.e. crystalline form VII, while also providing a preparation process for the crystalline form of agomelatine. When compared with crystalline form II of the currently available Valdoxan, the said new crystalline form offers valuable characteristics and a preparation method having good reproducibility.

The crystalline form VII of agomelatine in the present invention may be used in the treatment of diseases of the melatoninergic system, sleep disorders, stress, anxiety, seasonal affective disorder, severe depression, cardiovascular diseases, digestive system diseases, insomnia and fatigue brought on by jet lag, schizophrenia, phobias, and depression.

The present invention also aims to provide a method of preparation for the crystalline form VII of agomelatine which is simple in its operation and offers good reproducibility.

A further aim of the present invention is to provide a pharmaceutical composition, which includes the crystalline form VII of agomelatine of this invention as well as pharmaceutically acceptable adjuvants or excipients.

The said pharmaceutical composition can be configured to be used in different application routes, especially when administered either orally or via injection.

According to the nature and severity of the illness, treatment may be administered via a regulated dosage based on the age and weight of the patient. The dosage may vary between 0.1 mg and 1 g per day, being administered once only or several times.

The following examples of X-ray diffraction diagrams of the crystalline form of agomelatine of the present invention use Bragg angle 2θ, interplanar crystal spacing d and relative intensity to show:

| 2θ° | d(Å) | Relative intensity (I %) |
|---|---|---|
| 10.557 | 8.3725 | 32.35 |
| 13.301 | 6.6509 | 11.45 |
| 16.145 | 5.4855 | 10.60 |
| 17.286 | 5.1258 | 6.19 |
| 17.841 | 4.9675 | 100.00 |
| 19.359 | 4.5813 | 10.83 |
| 20.089 | 4.4164 | 11.77 |
| 23.366 | 3.8040 | 29.82 |
| 24.944 | 3.5667 | 21.60 |
| 26.128 | 3.4078 | 12.47 |

When using X-ray diffraction to measure the crystallization of the present invention, sometimes owing to the measurement equipment or test conditions, the measured peaks show slight deviations in measurement; more specifically, for example there may be a deviation in measurement of the 2θ value by approximately ±0.2; even if extremely accurate equipment is used, a deviation of approximately ±0.1 may be seen. As a result, this deviation must be taken into consideration when determining each crystalline structure.

XRD Test Conditions:
  Instrument model: Bruker D8 ADVANCE X-ray diffractometer
  Experiment parameters:
  Detector: LynxEye detector
  Light source: CuKα 40 kV 40 mA
  Monochromator: Ni filter disc
  Divergence slit: 1°
  DivH.L.Slit: 1.0 mm
  Probe: LynxEye probe
  Scanning method: θ-θ continuous scanning
  Scanning range: 3°~45°
  Step length: 0.02°
  Scanning speed: 8.0°/min
  Scanning time: 5 min
  Scanning temperature: Room temperature
DSC Test Conditions:
  Instrument model: NETZSCH DSC 204F1
  Experimental conditions:
  Crucible type: Standard aluminium crucible (perforated)
  Sweep gas: high purity nitrogen 20 ml/min; shielding gas: high purity nitrogen 60 ml/min.
  Temperature range: Room temperature~140° C.
  Heating rate: 10° C./min
TGA Test Conditions
  Instrument model: NETZSCH TG 209F1
  Experimental conditions:
  Crucible type: $Al_2O_3$
  Sweep gas: $N_2$ 20 ml/min, shielding gas: $N_2$ 10 ml/min
  Temperature range: Room temperature~300° C.
  Heating rate: 10° C./min The method of preparation of the crystalline form VII of the present invention involves dissolving agomelatine compounds of formula (II) or (III) in acetic acid, to which acetate is then added (preferably potassium acetate or ammonium acetate). Water is then added dropwise to this reaction mixture and agitated at a temperature of 17-23° C. in order to bring about crystallization, with the crystals then being separated from the solution.

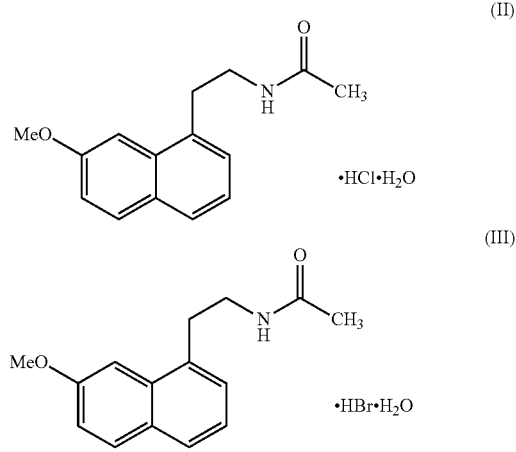

In the present invention as described, there are no special requirements in terms of the amount of acetic acid that is to be added as long as a sufficient amount is used to dissolve the raw materials, while heating can also be suitably applied to facilitate dissolution.

The molar ratio of agomelatine compounds of form (II) or (III) and acetate is preferably in the order of 1:1-1.5, most optimally 1:1-1.1. The said acetate comprises potassium acetate and ammonium acetate.

In the preparation method of the present invention as described, the ratio of volume of acetic acid to water is 1:10-30.

In a preferred embodiment of the preparation method for the crystalline form VII in the present invention, when the temperature of the resulting reaction mixture reaches 19-25° C., and in particular when around 22° C. or 23° C., water is added dropwise in order to bring about crystallization.

In a further preferred embodiment, when water is added dropwise to the resulting reaction mixture, agitation then occurs at a temperature of around 20° C. This may take place over a period of around 2 hours in order to bring about crystallization.

In another preferred embodiment, following the addition of acetate, the reaction mixture is heated to 30-50° C., resulting in a clear solution; the said solution is then left to cool on its own, and water is added dropwise in order to bring about crystallization.

The present invention results in a new crystalline form VII of agomelatine, with high purity, stable crystalline form and good reproducibility making it easy to mass-produce, thus possessing advantages in production. Compared to the currently available crystalline forms, it possesses the qualities of good stability and solubility.

According to Chinese patent applications CN 201010126254.X and CN 201010126263.9, agomelatine compounds of formula (II) or (III) as previously described may be produced by means of the following preparation method, where the said preparation method involves reacting agomelatine with various forms of HCl or HBr in order to form a hydrate. The two methods are as follows: Agomelatine is firstly dissolved in a water-containing organic solvent, after which either HCl or HBr gas is added, the solid crystals are washed and then dried; or else agomelatine is added to a solvent containing HCl or HBr, and the solid crystals are then washed and dried. If the first method is used, an overabundance of HCl or HBr may lead to a decrease in yield, while in the second method the amount of HCl and HBr present in the solvent is easily controlled. Therefore the second method is preferred.

Specifically, agomelatine may be added to a water-containing organic solvent, followed by the addition of a solvent containing HCl or HBr dropwise. The solid crystals are then washed and then dried.

Likewise, it is also possible to add agomelatine to an organic solvent, followed by the addition of an aqueous solution containing HCl or HBr dropwise. The solid crystals are then washed and then dried.

The full contents of reference documents either quoted or mentioned in this application have been referenced.

DETAILS OF THE EMBODIMENTS

Figure 1:
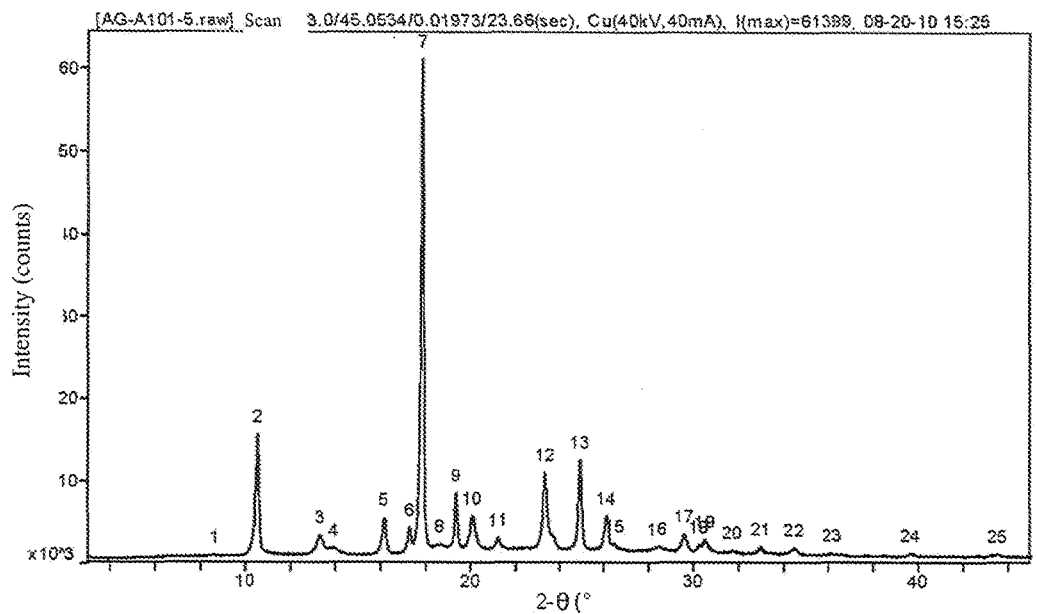
FIG. 1 shows the X-ray diffraction of the crystalline form VII in embodiment 1 of the present invention.
Figure 2:
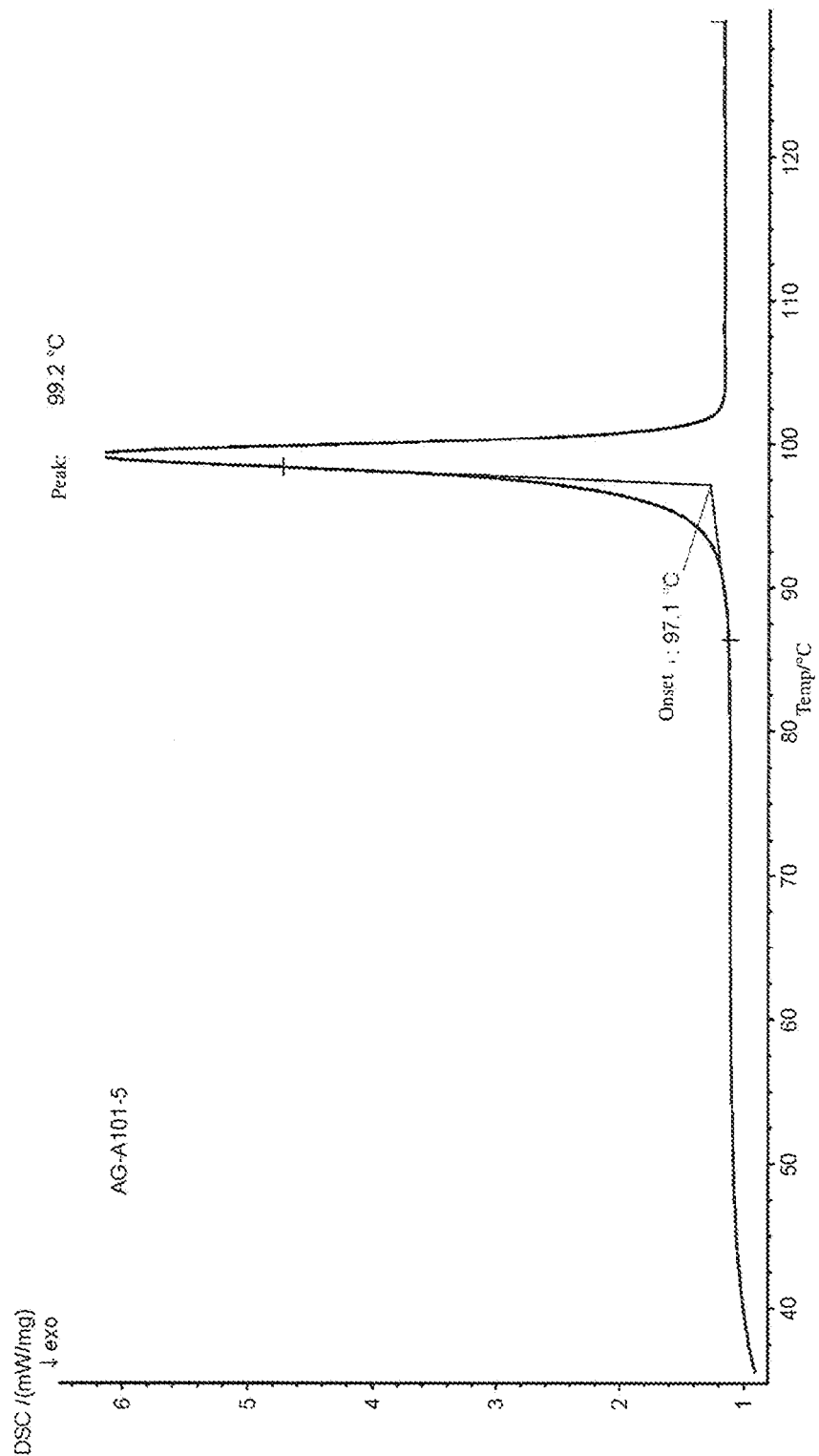
FIG. 2 shows the DSC change in heat absorption of the crystalline form VII in embodiment 1 of the present invention.

The following embodiments further describe the present invention but do not limit the scope thereof.

Embodiment 1

7.6 g of agomelatine compound of formula (III) is dissolved in 19 ml of AcOH, to which 3.5 g of KOAc is added; the mixture is then heated to 40° C., resulting in a clear solution; this is then left to cool on its own, gradually becoming turbid. When the temperature reaches 22° C., 250 ml water is added dropwise. At a temperature of ~20° C., agitation is carried out over 2 hours, followed by filtration, then washing and drying the filter cake at 50° C. under vacuum until constant weight is achieved, resulting in 4.5 g of white solid, purity: 99.8%, melting point: 98-100° C.

Embodiment 2

2 g of agomelatine compound of formula (II) is dissolved in 5 ml of AcOH, to which 0.57 g of NH$_4$OAc is then added; the mixture is then heated to 40° C., resulting in a clear solution; this is then left to cool on its own, gradually becoming turbid; when the temperature reaches 22° C., 150 ml of water is added dropwise, and at a temperature of ~20° C., agitation is carried out over 2 hours, followed by filtration, then washing and drying the filter cake at 50° C. under vacuum until constant weight is achieved, resulting in 1.4 g of white solid, purity: 99.7%, melting point: 98-100° C.

Embodiment 3

40 g of agomelatine compound of formula (III) is dissolved in 130 ml of AcOH, to which 10 g of NH$_4$OAc is then added; the mixture is then heated to 40° C., resulting in a clear solution; this is then left to cool on its own, gradually becoming turbid; when the temperature reaches 23° C., 2.6 L of water is added dropwise, and at a temperature of ~20° C., agitation is carried out over 2 hours, followed by filtration, then washing and drying the filter cake at 50° C. under vacuum until constant weight is achieved, resulting in 25 g of white solid, purity: 99.8%, melting point: 98-100° C.

Embodiment 4

Crystalline forms II, III, VI and VII (obtained through embodiment 3) are each placed in thermostatic containers at a temperature of 40° C. and stored for 20 days, with the stability of these crystalline samples being studied using the method of High Performance Liquid Chromatography.

1. Purity Measurement of the Sample

Chromatographic conditions: Octadecyl silane chemically bonded silica is used as packing; a mixed solution of 10 mmol/L phosphate buffer (adjusted to pH 7.0 with sodium hydroxide) and acetonitrile in the ratio 2:7 by volume acts as the mobile phase; column temperature 40° C.; and detection wavelength 220 nm. Purity is measured using an internal standard method.

In the mobile phase, crystalline forms II, III, VI and VII are distributed into 1 mg/mL solutions, 10 μL of each of which are then passed into a liquid chromatograph, with their chromatograms being recorded.

2. Assay of the Sample

The reference sample purity measurement method was used, with measurements being made using an external standard method, the results are shown in Table I.

TABLE I

| | Sample name | | | | | | | |
|---|---|---|---|---|---|---|---|---|
| | Crystalline form II | | Crystalline form III | | Crystalline form VI | | Crystalline form VII | |
| | Purity | Content | Purity | Content | Purity | Content | Purity | Content |
| Before storage | 99.7% | 99.5% | 99.9% | 99.5% | 99.7% | 99.3% | 99.8% | 99.8% |
| After storage in the thermostatically controlled containers for 20 days | 99.3% | 99.6% | 99.3% | 99.4% | 99.6% | 99.1% | 99.7% | 99.6% |

3. Measurement of Water Solubility

The HPLC method was used to determine water solubility, with measurements being made using an external standard method. The results are shown in Table II.

TABLE II

| | Sample name | | |
|---|---|---|---|
| | Crystalline form II | Crystalline form VI | Crystalline form VII |
| Solubility (mg/ml) | 0.301 | 0.336 | 0.330 |

4. Determination of Crystalline Stability

Measured using the pharmacopoeia stability assessment method:

1) Influencing factor testing (exposed for 10 days): high temperature (60° C.), illumination (4500 lx), high humidity (92.5% RH, 25° C.)

2) Accelerated testing (hermetically sealed for 6 months): temperature 40° C., humidity 75% RH 3) Long term testing (hermetically sealed for 12 months): temperature 25° C., humidity 60% RH

TABLE III

| | | Sample name | | |
|---|---|---|---|---|
| | | Crystalline form II | Crystalline form VI | Crystalline form VII |
| Influencing factor | High temperature | ✓* | x* | ✓ |
| | Illumination | ✓ | ✓ | ✓ |
| | High humidity | ✓ | ✓ | ✓ |
| Accelerated testing | | ✓ | ✓ | ✓ |
| Long term testing (6 months) | | ✓ | ✓ | ✓ |
| Long term testing (9 months) | | ✓ | ✓ | ✓ |
| Long term testing (12 months) | | ✓ | x | ✓ |

*✓ - stable;
x - unstable

As can be seen from the test results, in its preparation process, the stability and purity of the new crystalline form VII of agomelatine clearly offers advantages when compared with currently available crystalline forms, especially in pharmaceutical production.

5. Study into the Stability of Pharmaceutical Compositions (Crystalline Form, Purity and Content)

The product (obtained via embodiment 7) was subjected to the pharmacopoeia stability assessment method and underwent influencing factor testing (10 day exposure): High temperature (40° C.), illumination (4500 lx), high humidity (92.5% RH, 25° C.); Accelerated testing (hermetically sealed for 6 months): temperature 40° C., humidity 75% RH, Long term testing (hermetically sealed for 8 months): temperature 25° C., humidity 60% RH. The assessment results demonstrate that under the above conditions neither the crystalline form, purity nor content of the product underwent any changes.

Consequently, the test results of the pharmaceutical ingredients and capsules of this product indicate that form VII has a great potential in pharmaceutical production.

Embodiment 5

Agomelatine Compound of Formula (II)

Figure 3:
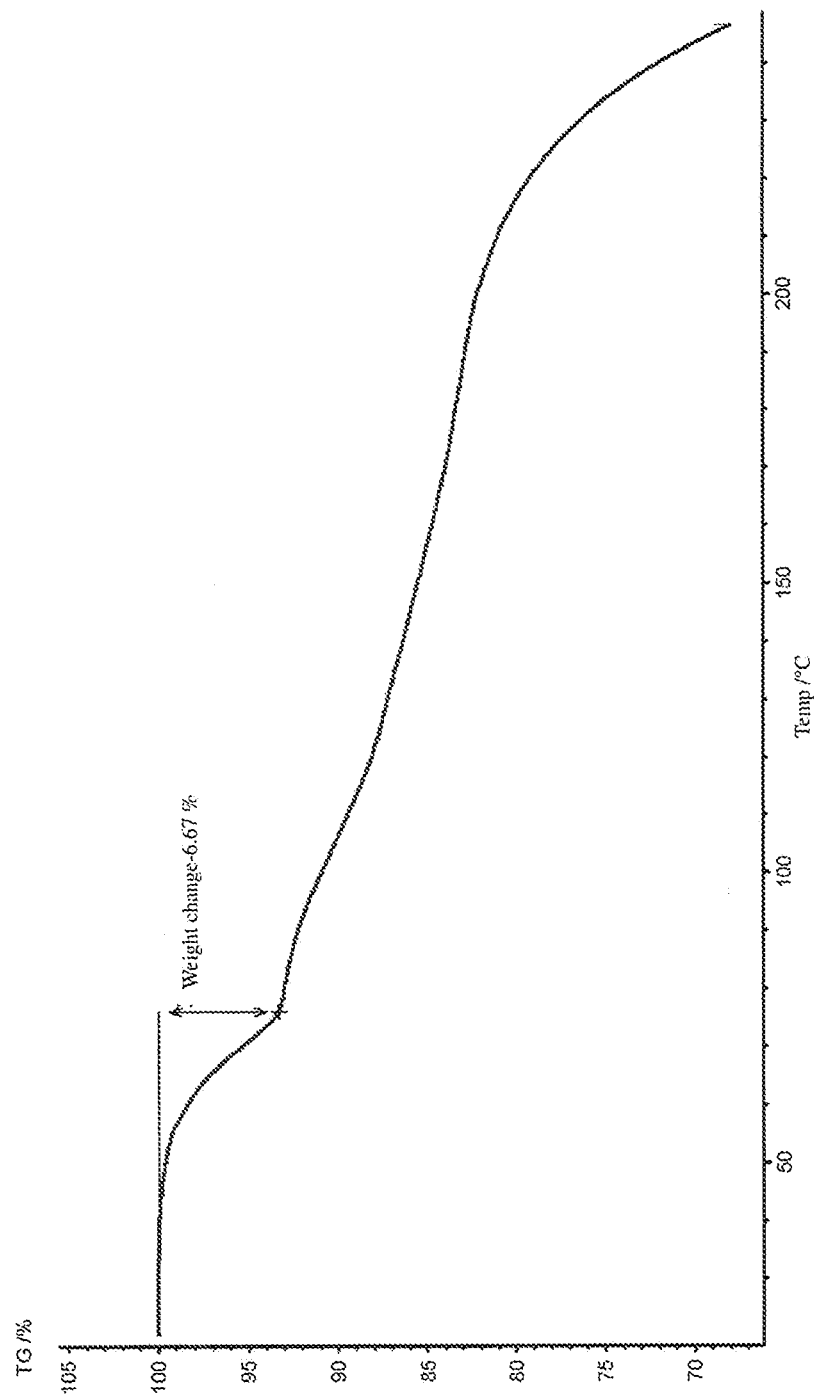
FIG. 3 shows the thermogravimetric analysis TGA curve of the product in embodiment 5 of the present invention.

10 g of agomelatine is added to a 100 ml solution of ethyl acetate. At a temperature of 10° C., 4.6 g of an aqueous solution of HCl (36%) is slowly added dropwise. Agitation is then carried out for 1 hour, followed by filtration and the resulting solid is washed twice in 10 ml of ethyl acetate, then dried at a temperature of 40° C. to obtain 10.2 g of form II white solid; purity: 99.8%, yield: 88.7%.
Cl Elemental Analysis:
 Theoretically calculated value: Cl content 11.91 wt %
 Measured Value: Cl Content 11.86 wt %
Determination of Crystal Water Content of Agomelatine Compound of Formula (II):
 The calculated theoretical crystal water content of $C_{15}H_{17}NO_2 \cdot HCl \cdot H_2O$ is 6.06 wt %.
 5.1 The Fischer Method (*Chinese Pharmacopoeia* 2010 Edition, Appendix VIII M)
 The product resulting from embodiment 5 was measured according to the Fischer method as mentioned above, and the crystal water content recorded was: 6.15 wt %.
 5.2 Thermogravimetric Analysis (*Chinese Pharmacopoeia* 2010 Edition, Appendix VIII Q)
 The product resulting from embodiment 5 was measured according to thermogravimetric analysis as mentioned above, and the loss of crystal water recorded was: 6.67 wt %, i.e. the crystal water content of the original product was 6.67 wt %. For TGA curve, please refer to FIG. 3.

Embodiment 6

Agomelatine Compound of Formula (III)

Figure 4:
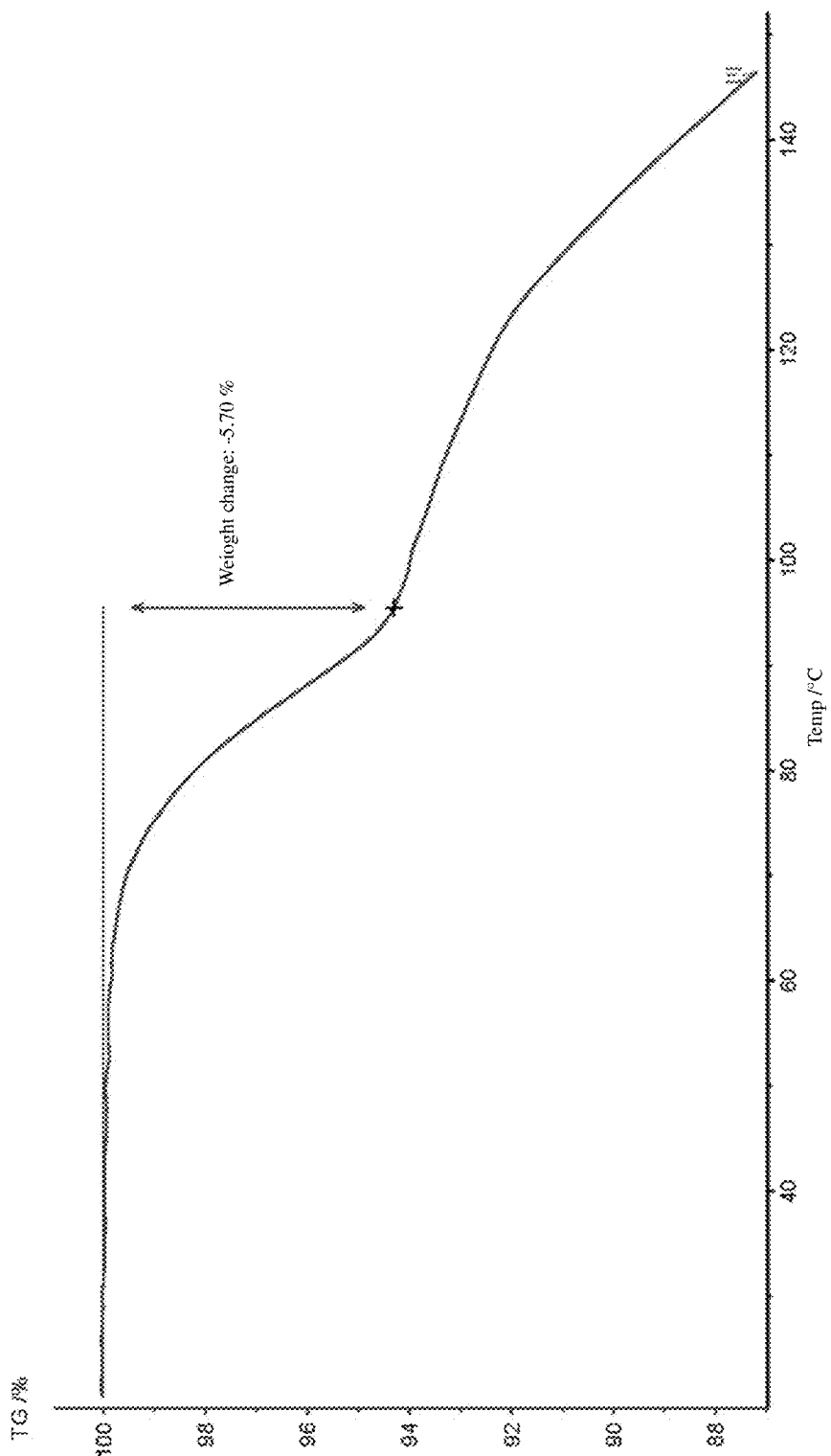
FIG. 4 shows the thermogravimetric analysis TGA curve of the product in embodiment 6 of the present invention.

100 g of agomelatine is stirred and dissolved in 800 ml of ethyl acetate. At a low temperature an aqueous solution of HBr (8.32 g, 40%) is added dropwise and then agitated for 1 hour before being filtered. The resulting solid is then washed twice in 100 ml of ethyl acetate, then dried at a temperature of 40° C. to obtain 120 g of white solid; purity 99.9%, yield: 85.3%.
Analysis Results ($C_{15}H_{17}NO_2 \cdot HBr \cdot H_2O$)
 Calculated value: Br % (23.35%)
 Measured value: Br % (23.29%)
Determination of Crystal Water Content of Agomelatine Compound of Formula (III):
 The calculated theoretical crystal water content of $C_{15}H_{17}NO_2 \cdot HBr \cdot H_2O$ is 5.26 wt %.
 6.1 The Fischer Method (*Chinese Pharmacopoeia* 2010 Edition, Appendix VIII M)
 The product resulting from embodiment 6 was measured according to the Fischer method as mentioned above, and the crystal water content recorded was: 5.10 wt %.
 6.2 Thermogravimetric Analysis (*Chinese Pharmacopoeia* 2010 Edition, Appendix VIII Q)
 The product resulting from embodiment 6 was measured according to thermogravimetric analysis as mentioned above, and the loss of crystal water recorded was: 5.70 wt %, i.e. the crystal water content of the original product was 5.70 wt %. For TGA curve, please refer to FIG. 4.

Embodiment 7

Preparation of Pharmaceutical Composition

| 1000 capsules prescribed (dosage: 25 mg) | |
|---|---|
| Crystalline form VII | 25 g |
| Lactose (Spherolac 100) | 88.9 g |
| Magnesium stearate | 1.7 g |
| Starch (Starch 1500) | 25.5 g |
| Sodium carboxymethyl starch (CMS-Na) | 8.5 g |
| Ac-Di-Sol ® (FMC) | 17 g |
| Stearic acid | 3.4 g |

The invention claimed is:
1. A crystalline form VII of agomelatine, characterized by the following X-ray diffraction diagram expressed in terms of interplanar crystal spacing d, Bragg angle 2θ and relative intensity:

| 2θ° | d(Å) | Relative intensity (I %) |
|---|---|---|
| 10.557 ± 0.2 | 8.3725 | 32.35 |
| 13.301 ± 0.2 | 6.6509 | 11.45 |
| 16.145 ± 0.2 | 5.4855 | 10.60 |
| 17.286 ± 0.2 | 5.1258 | 6.19 |
| 17.841 ± 0.2 | 4.9675 | 100.00 |
| 19.359 ± 0.2 | 4.5813 | 10.83 |
| 20.089 ± 0.2 | 4.4164 | 11.77 |
| 23.366 ± 0.2 | 3.8040 | 29.82 |

| 2θ° | d(Å) | Relative intensity (I %) |
|---|---|---|
| 24.944 ± 0.2 | 3.5667 | 21.60 |
| 26.128 ± 0.2 | 3.4078 | 12.47. |

2. A preparation method for the crystalline form of claim 1, wherein an agomelatine compound of formula (II) or (III)

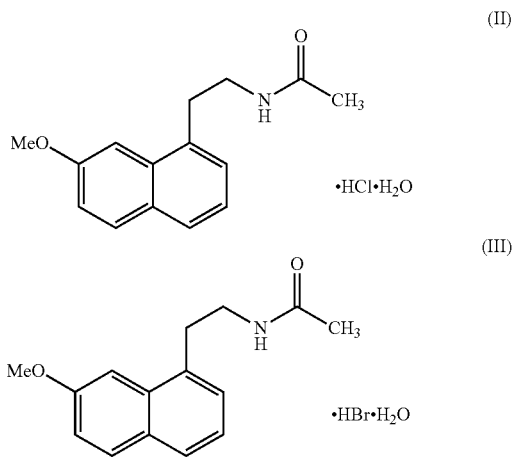

is dissolved in acetic acid, to which acetate is then added, followed by the addition of water dropwise to this reaction mixture, which is then agitated at a temperature of 17-23° C. in order to bring about crystallization, with the crystals then being separated from the solution.

3. The preparation method according to claim 2, wherein the molar ratio of the agomelatine compound of formula (II) or (III) and acetate is from 1:1-1.5.

4. The preparation method according to claim 3, wherein the molar ratio of the agomelatine compound of formula (II) or (III) and acetate is from 1:1-1.1.

5. The preparation method according to claim 2, wherein the ratio of volume of acetic acid to water is 1:10-30.

6. The preparation method according to claim 2, wherein the acetate is potassium acetate or ammonium acetate.

7. The preparation method according to claim 2, wherein when the temperature of the resulting reaction mixture reaches 19-25° C., water is added dropwise in order to bring about crystallization.

8. The preparation method according to claim 7, wherein when the temperature of the resulting reaction mixture reaches 22° C. or 23° C., water is added dropwise in order to bring about crystallization.

9. The preparation method according to claim 2, wherein water is added dropwise to the resulting reaction mixture which is then agitated at a temperature of 20° C. in order to bring about crystallization.

10. The preparation method according to claim 2, wherein following the addition of the acetate, the reaction mixture is heated to 30-50° C., resulting in a clear solution; the solution is then left to cool on its own, and water is added dropwise in order to bring about crystallization.

11. A pharmaceutical composition comprising the crystalline form of agomelatine according to claim 1 in combination with one or more pharmaceutically acceptable adjuvants or excipients.

12. A method of treating a condition selected from sleep disorders, stress, anxiety, seasonal affective disorder, severe depression, cardiovascular diseases, digestive system diseases, insomnia and fatigue brought on by jet lag, schizophrenia, phobias, and depression in a subject in need thereof, comprising administration of an effective amount of the crystalline form of agomelatine according to claim 1.

* * * * *